(12) United States Patent
Anderson et al.

(10) Patent No.: US 11,324,958 B2
(45) Date of Patent: May 10, 2022

(54) SYSTEM AND METHOD OF TESTING DEFIBRILLATOR ELECTRODES

(71) Applicant: HeartSine Technologies Limited, Belfast (GB)

(72) Inventors: Johnny Anderson, Belfast (GB); Allister McIntyre, Belfast (GB)

(73) Assignee: Heartsine Technologies Limited, Belfast (GB)

(*) Notice: Subject to any disclaimer, the term of this patent is extended or adjusted under 35 U.S.C. 154(b) by 312 days.

(21) Appl. No.: 15/989,418

(22) Filed: May 25, 2018

(65) Prior Publication Data

US 2018/0369597 A1 Dec. 27, 2018

(30) Foreign Application Priority Data

May 25, 2017 (GB) ...................................... 1708354

(51) Int. Cl.
| | | |
|---|---|---|
| *A61N 1/04* | (2006.01) | |
| *A61N 1/08* | (2006.01) | |
| *A61N 1/372* | (2006.01) | |
| *A61N 1/39* | (2006.01) | |

(52) U.S. Cl.
CPC ......... *A61N 1/37241* (2013.01); *A61N 1/046* (2013.01); *A61N 1/0492* (2013.01); *A61N 1/3931* (2013.01); *A61N 1/3937* (2013.01); *A61N 2001/083* (2013.01); *A61N 2001/37294* (2013.01)

(58) Field of Classification Search
CPC .............. A61N 1/37241; A61N 1/0492; A61N 1/3937; A61N 1/3931; A61N 1/046; A61N 1/3904; A61N 1/3925; A61N 2001/083; A61N 2001/37294
USPC .................................... 600/372, 382; 607/28
See application file for complete search history.

(56) References Cited

U.S. PATENT DOCUMENTS

| | | | | |
|---|---|---|---|---|
| 4,785,812 A | * | 11/1988 | Pihl ...................... | A61N 1/3931 607/8 |
| 5,700,281 A | * | 12/1997 | Brewer ................ | A61N 1/3931 607/5 |
| 7,526,345 B2 | * | 4/2009 | Covey .................. | A61N 1/0492 607/142 |
| 2003/0055478 A1 | * | 3/2003 | Lyster .................. | A61N 1/0492 607/142 |

(Continued)

*Primary Examiner* — Carl H Layno
*Assistant Examiner* — Anh-Khoa N Dinh

(57) ABSTRACT

An electrode test system of a defibrillator including electrodes in a face-to-face test arrangement forming a capacitor, an impedance measurement signal generator connected to the electrodes and configured to send an ac signal to the electrodes, an impedance measurement signal processor connected to the electrodes which is placeable in an electrode test state and configured to receive an electrode test ac signal from the electrodes and process the electrode test ac signal to obtain a processed electrode test ac signal, a defibrillator processor connected to the impedance measurement signal generator and the impedance measurement signal processor configured to place the impedance measurement signal processor in the electrode test state and to receive the processed electrode test ac signal, analyze the processed electrode test ac signal to obtain an electrode test impedance signal and analyze the electrode test impedance signal to determine a pass condition or a fail condition of the electrodes.

22 Claims, 2 Drawing Sheets

(56) References Cited

U.S. PATENT DOCUMENTS

2006/0142806 A1* 6/2006 Katzman ............. A61N 1/3904
607/5
2008/0051845 A1* 2/2008 Mentelos ............ A61B 5/0424
607/28

* cited by examiner

SYSTEM AND METHOD OF TESTING DEFIBRILLATOR ELECTRODES

PRIORITY INFORMATION

The present application claims priority to Great Britain Patent Application No. 1708354.4, filed May 25, 2017, the contents of which are incorporated herein in their entirety.

FIELD OF THE INVENTION

This disclosure relates to testing of electrodes for defibrillators, and particularly to the testing of connection of the electrodes to the defibrillator and the electrical integrity of the electrodes, i.e. the ability of the electrodes to conduct an electrical signal.

BACKGROUND

Defibrillators are used to provide a 'shock', i.e. electrical signals, to a patient's heart during a cardiac arrest. Studies have shown that the efficacy of a shock decreases significantly as time from the cardiac arrest increases. It is therefore important to use a defibrillator to apply electrical signals to the patient's heart as quickly as possible. This being the case, defibrillators are now frequently found in various public locations, not just in hospitals.

The defibrillator electrodes are generally housed in a pouch to protect them. Each electrode has a connecting wire which is connected to a plug in the defibrillator. In many locations, a defibrillator may not be used for substantial periods of time. It is crucial that the connectivity of the defibrillator electrodes, connecting wires and defibrillator plug, and the electrical integrity of the defibrillator electrodes, is maintained over these periods, or, if compromised, that this information is made available to a potential user of the defibrillator. This is particularly the case when a defibrillator may be used by a member of the public with little or no experience of defibrillator technology or operation. It is therefore desirable to provide defibrillators with a means by which the electrodes connectivity and integrity may be tested.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DESCRIPTION

Figure 1:
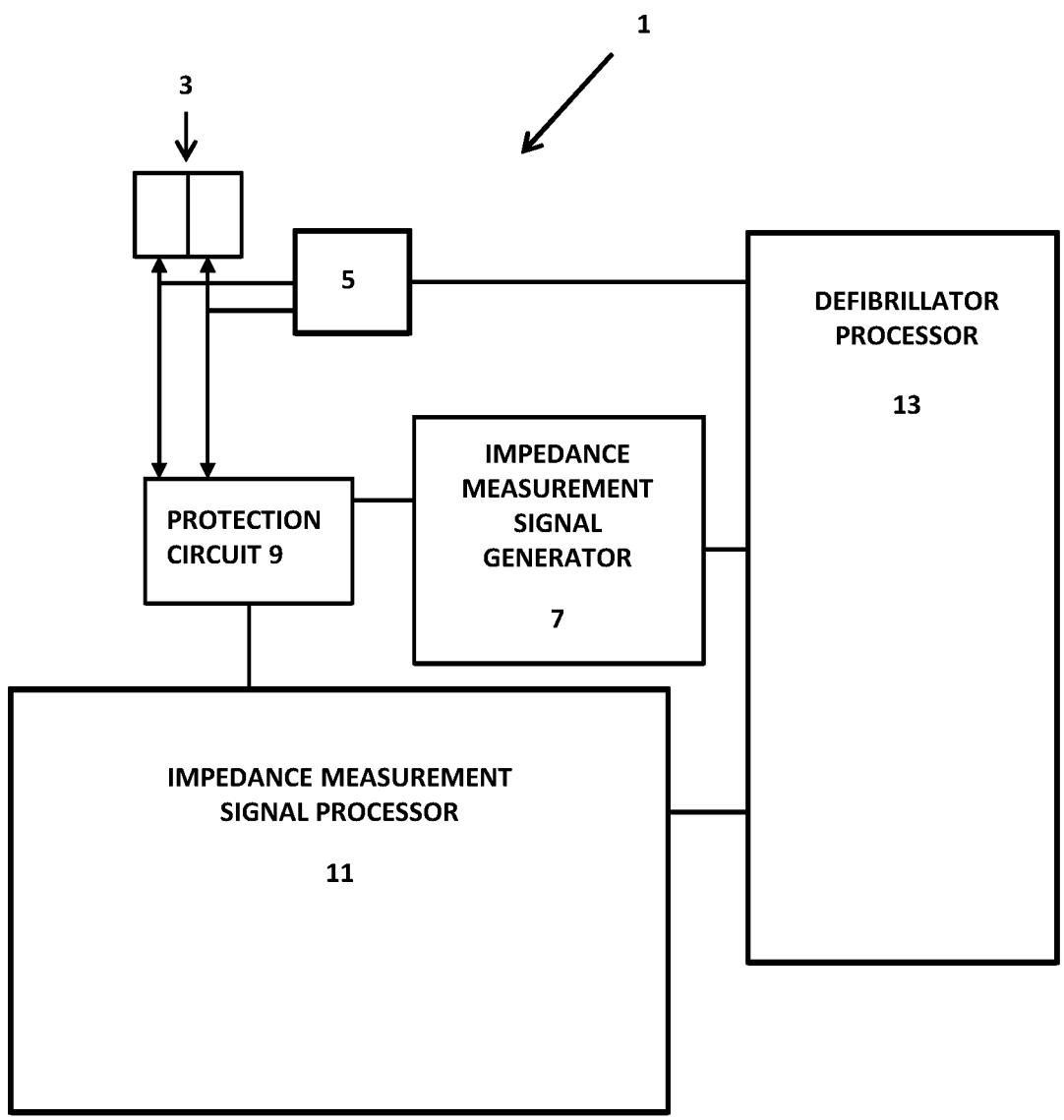
FIG. 1 is a schematic representation of an electrode test system of a defibrillator according to the first aspect of the disclosure.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, known details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Brief Overview

According to a first aspect of the disclosure, there is provided an electrode test system of a defibrillator including electrodes in a face-to-face test arrangement forming a capacitor, an impedance measurement signal generator connected to the electrodes and configured to send an ac signal to the electrodes, an impedance measurement signal processor connected to the electrodes which is placeable in an electrode test state and configured to receive an electrode test ac signal from the electrodes and process the electrode test ac signal to obtain a processed electrode test ac signal and a defibrillator processor connected to the impedance measurement signal generator and the impedance measurement signal processor. The defibrillator processor is configured to place the impedance measurement signal processor in the electrode test state and to receive the processed electrode test ac signal, to analyze the processed electrode test ac signal to obtain an electrode test impedance signal and to analyze the electrode test impedance signal to determine a pass condition or a fail condition of the electrodes.

Detailed Description

The present disclosure addresses the issues outlined above, and provides a defibrillator with a means by which the electrodes connectivity and integrity may be tested. According to a first aspect of the disclosure, an electrode test system of a defibrillator his disclosed which includes one or more of electrodes in a face-to-face test arrangement forming a capacitor, an impedance measurement signal generator connected to the electrodes and configured to send an ac signal to the electrodes, and an impedance measurement signal processor connected to the electrodes. The impedance measurement signal generator is placeable in an electrode test state and is configured to receive an electrode test ac signal from the electrodes and process the electrode test ac signal to obtain a processed electrode test ac signal. The system also includes a defibrillator processor connected to the impedance measurement signal generator and the impedance measurement signal processor. The defibrillator processor is configured to place the impedance measurement signal processor in the electrode test state and to receive the processed electrode test ac signal, analyse the processed electrode test ac signal to obtain an electrode test impedance signal and analyse the electrode test impedance signal to determine a pass condition or a fail condition of the electrodes. The defibrillator processor may be configured to send at least one control signal to the impedance measurement signal generator to cause the impedance measurement signal generator to send the ac signal to the electrodes.

The defibrillator processor may be configured to send at least one control signal to the impedance measurement signal processor to place the impedance measurement signal processor in the electrode test state. The defibrillator processor may be configured to send at least one control signal to the impedance measurement signal processor to adjust one or more characteristics thereof to place the impedance measurement signal processor in the electrode test state.

The impedance measurement signal processor may include an amplifier module and the defibrillator processor may be configured to send at least one control signal to the impedance measurement signal processor to adjust one or more characteristics of the amplifier module to place the impedance measurement signal processor in the electrode test state. The defibrillator processor may be configured to send at least one control signal to the impedance measurement signal processor to adjust a gain characteristic of the amplifier module to place the impedance measurement signal processor in the electrode test state.

The impedance measurement signal processor may include a signal conditioning module and the defibrillator processor may be configured to send at least one control signal to the impedance measurement signal processor to adjust one or more characteristics of the signal conditioning module to place the impedance measurement signal processor in the electrode test state. The defibrillator processor may be configured to send at least one control signal to the impedance measurement signal processor to adjust one or more conditioning function characteristics of the signal conditioning module to place the impedance measurement signal processor in the electrode test state. The signal conditioning module may include conditioning function characteristics for carrying out conditioning functions including any of filtering, analogue to digital conversion, signal processing.

The impedance measurement signal processor may include a memory unit and the defibrillator processor may be configured to send at least one control signal to the impedance measurement signal processor to adjust one or more control characteristics stored in the memory unit to place the impedance measurement signal processor in the electrode test state. The defibrillator processor may be configured to send at least one control signal to the impedance measurement signal processor to adjust one or more control characteristics stored in the memory unit which adjusts one or more characteristics of the amplifier module to place the impedance measurement signal processor in the electrode test state. The defibrillator processor may be configured to send at least one control signal to the impedance measurement signal processor to adjust one or more control characteristics stored in the memory unit which adjusts one or more characteristics of the signal conditioning module to place the impedance measurement signal processor in the electrode test state.

The amplifier module of the impedance measurement signal processor may be implemented in hardware. The signal conditioning module of the impedance measurement signal processor may be implemented in hardware. The amplifier module of the impedance measurement signal processor may be implemented in software. The signal conditioning module of the impedance measurement signal processor may be implemented in software. The amplifier module and the signal conditioning module may be implemented in separate software modules or the same software module.

Each electrode may be substantially planar and include at least one face. The at least one face of each electrode may be placed in the face-to-face test arrangement to form the capacitor. Each electrode may be substantially planar and include a first face and a second face. The first face of each electrode may be placed in the face-to-face test arrangement to form the capacitor. The first face of each electrode may be provided by a dielectric liner of the electrode. The dielectric liners of the electrodes may be substantially adjacent in the electrodes face-to-face test arrangement to form the capacitor. A further dielectric may be provided by one or more air gaps between the substantially adjacent dielectrics in the electrodes face-to-face test arrangement.

Alternatively, the second face of each electrode may be placed in the face-to-face test arrangement to form the capacitor. The second face of each electrode may be provided by a substrate of the electrode. Alternatively, the first face of a first electrode and the second face of a second electrode may be placed in the face-to-face test arrangement to form the capacitor.

A first electrode may include a conductor and a dielectric liner and a second electrode may include a conductor. The second electrode conductor may be substantially adjacent to the first electrode dielectric liner in the electrodes face-to-face test arrangement to form the capacitor. The electrodes may each include a conductor. A dielectric may be placed between the conductors in the electrodes face-to-face test arrangement to form the capacitor.

Each electrode may include a substrate having a first face and a second face, a conductor having a first face attached to the second face of the substrate and a second face, a gel element having a first face attached to the second face of the conductor and a second face, and a dielectric liner having a first face attached to the second face of the gel element and a second face.

The substrate may include a plastic material, particularly a substantially transparent plastic material. The substrate may include a foam material.

The conductor may be printed onto the second face of the substrate. The conductor may include silver ink. The conductor may include tin.

The dielectric liner may be a release liner which is removed on use of the electrode. The dielectric liner of each electrode may be joined together and folded to be substantially adjacent in the electrodes face-to-face test arrangement.

The electrodes may be located in a face-to-face test arrangement within a pouch.

The impedance measurement signal generator may be configured to generate the ac signal at a pre-determined voltage. The ac signal may include any of a sine wave, a square wave. The ac signal may have a frequency in the range of approximately 30 kHz to approximately 64 kHz, preferably approximately 32 kHz. Further the ac signal can also be in a larger range such as between 5 KHz and 80 KHz.

The defibrillator processor may be configured to determine a pass condition if the electrode test impedance signal is within a pre-determined pass range and a fail condition if the electrode test impedance signal is above the pre-determined pass range. The pass range may be pre-determined by assessing an expected range of values of the electrode test impedance signal when connectivity and electrical integrity of the electrodes is acceptable. The pre-determined pass range may be approximately 1 kΩ to approximately 5 kΩ. The pre-determined pass range may be determined by testing of defibrillator electrodes in various states of connectivity and electrical integrity. The pre-determined pass range may be different for different types of defibrillator electrodes. When the electrodes are in a fail condition, a signal indicating an open circuit may be received by the defibrillator processor.

The defibrillator may include a protection circuit connected between the electrodes and the impedance measurement signal generator and the impedance measurement signal processor to protect them against receiving a defibrillator shock signal.

An electrode test may be carried out as part of an automatic defibrillator self-test process. An electrode test may be carried out at regular intervals. The regular intervals may include any of once a day, once a week, once a month. An electrode test may be carried out on power-up of the defibrillator. An electrode test may be carried out before application of a shock to a patient. An electrode test may be carried out on initiation by a user of the defibrillator, for example by activating a switch on the defibrillator.

After an electrode test, when the defibrillator processor determines a pass condition for the electrodes, the defibrillator processor may be configured to further analyse the electrode test impedance signal to determine an approximate age of the electrodes.

The defibrillator processor may compare the electrode test impedance signal with pre-determined ranges for the electrode test impedance signal to determine an approximate age of the electrodes. The pre-determined ranges may indicate, for example, electrodes of less than approximately 1 year of age, electrodes between approximately 1 year and approximately 2 years of age, electrodes between approximately 2 years and approximately 3 years of age, electrodes between approximately 3 years and approximately 4 years of age, electrodes of over approximately 4 years of age. Determination of an approximate age of the electrodes is possible because, as the electrodes get older, their gel dries out and capacitance of the electrodes changes.

The defibrillator may issue a message indicating an electrode pass condition or an electrode fail condition. This may include any of an audible message, a visible message.

According to a second aspect of the disclosure there is provided a method of testing electrodes of a defibrillator including placing electrodes in a face-to-face test arrangement to form a capacitor, using an impedance measurement signal generator to send an ac signal to the electrodes, using an impedance measurement signal processor placeable in an electrode test state to receive an electrode test ac signal from the electrodes and to process the electrode test ac signal to obtain a processed electrode test ac signal, and using a defibrillator processor to place the impedance measurement signal processor in the electrode test state and to receive the electrode test ac signal, to analyze the processed electrode test ac signal to obtain an electrode test impedance signal and to analyze the electrode test impedance signal to determine a pass condition or a fail condition of the electrodes.

FIG. 1 illustrates a defibrillator 1 including electrodes 3, a defibrillation signal generator 5, an impedance measurement signal generator 7, a protection circuit 9, an impedance measurement signal processor 11 and a defibrillator processor 13.

The impedance measurement signal generator 7 is configured to generate an ac signal at a pre-determined voltage. The ac signal includes a sine wave or a square wave and has a frequency in the range of approximately 30 kHz to approximately 64 kHz, preferably approximately 32 kHz. The ac signal is sent to the electrodes 3 and is used to test the electrodes 3. Signals having the same characteristics can be sent to the electrodes 3 in the measurement of an impedance of a patient connected to the electrodes 3.

The protection circuit 9 is a defibrillator signal protection circuit. This is configured to protect the impedance measurement signal generator 7 and the impedance measurement signal processor 11 against receiving a defibrillator shock signal, which would otherwise damage them.

The impedance measurement signal processor 11 includes an amplifier module, a signal conditioning module and a memory unit (not shown). The amplifier module includes a gain characteristic which is adjustable to place the impedance measurement signal processor 11 in an electrode test state. The signal conditioning module includes conditioning function characteristics, such as filtering ranges, ADC sample rate, resolution etc., which are adjustable to place the impedance measurement signal processor in the electrode test state. The signal conditioning module carries out conditioning functions including, at least, filtering, analogue to digital conversion and signal processing. The memory unit stores control characteristics which are adjustable for the adjustment of the characteristics of the amplifier module and the signal conditioning module.

In this example of the disclosure, the amplifier module and the signal conditioning modules of the impedance measurement signal processor 11 are implemented in hardware.

The defibrillator processor 13 includes a microprocessor. The defibrillator processor 13 is configured to send at least one control signal to the impedance measurement signal generator 7 to cause the generator 7 to send the ac signal to the electrodes 3. The defibrillator processor 13 is further configured to send control signals to the memory unit of the impedance measurement signal processor 11 to control adjustment of the characteristics of the modules of the impedance measurement signal processor 11.

In this example, the defibrillator 1 further includes a battery (not shown) which provides power for the components of the defibrillator. The various components of the defibrillator 1 are connected together as shown in the drawing, for sending and receiving signals between the components. It will be appreciated that other connections which are not shown may be provided between the components of the defibrillator 1.

Figure 2:
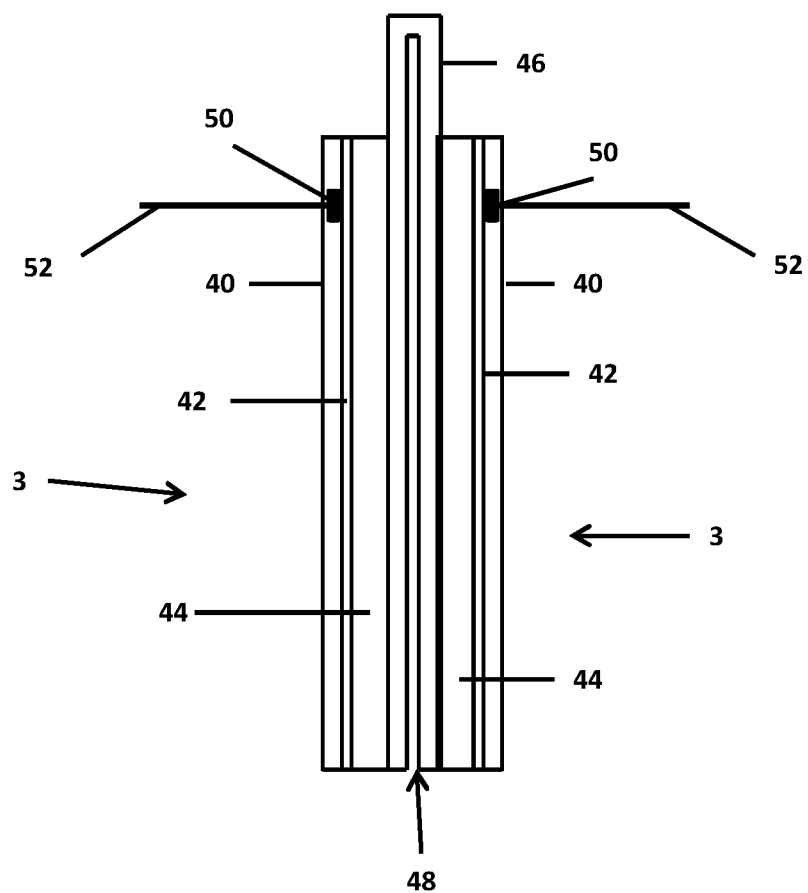
FIG. 2 is a schematic representation of electrodes of the defibrillator of FIG. 1.

Referring to FIG. 2, each of the electrodes 3 of the defibrillator 1 of FIG. 1 is substantially planar and includes a substrate 40, a conductor 42, a gel element 44 and a dielectric liner 46. The substrate 40 has a first face and a second face, the conductor 42 has a first face attached to the second face of the substrate 40 and a second face, the gel element 44 has a first face attached to the second face of the conductor 42 and a second face, and the dielectric liner 46 has a first face attached to the second face of the gel element 44 and a second face, as shown.

The substrate 40 includes a substantially transparent plastic material. The conductor 42 includes silver ink printed onto the second face of the substrate 40. The dielectric liner 46 of the electrodes is joined together and folded, as shown. The dielectric liner 46 is a release liner which is removed on use of the electrodes 3.

The electrodes 3 are located within a pouch (not shown). Each electrode 3 includes a connector stud 50 and a connecting wire 52, for connection of the electrode to a plug of the defibrillator 1.

In this embodiment, the electrodes 3 each include a conductor 42 and a dielectric in the form of a folded dielectric liner 46. Each electrode includes a first face provided by the dielectric liner 46 of the electrodes and a second face provided by a substrate 40 of the electrodes. The first face of each electrode, including the second face of the dielectric liner 46, is placed in the face-to-face test arrangement to form the capacitor. The electrodes 3 are in a face-to-face test arrangement, with parts of the dielectric liner 46 substantially adjacent to form the capacitor. A further dielectric is provided in the form of an air gap 48 between the substantially adjacent dielectric liner 46 in the electrodes face-to-face test arrangement. It will be appreciated that the air gap may be replaced by air pockets or may not be present. It will be appreciated that the second face of each electrode, provided by the substrate of the electrode, may be placed in the face-to-face test arrangement to form the capacitor. It will further be appreciated that the first face of a first electrode and the second face of a second electrode may be placed in the face-to-face test arrangement to form the capacitor.

In order to use the defibrillator 1 to apply defibrillation signals to a patient's heart, the electrodes 3 must have adequate connectivity and electrical integrity, i.e. the ability to conduct an electrical signal. This is determined by testing the electrodes 3 by applying an ac signal to the electrodes 3, receiving an electrode test ac signal from the electrodes 3, analyzing the electrode test ac signal to obtain the electrode test impedance signal and processing the electrode test impedance signal to determine a pass condition or a fail condition of the electrodes. Testing of the electrodes 3 is carried out using the impedance measurement signal generator 7 and the impedance measurement signal analyzer 11, i.e. equipment already present in the defibrillator 1.

When an electrode test is carried out, in this embodiment, the electrodes 3 are in their pouch, in a face-to-face test arrangement forming a capacitor.

The defibrillator processor 13 sends at least one control signal to the memory unit of the impedance measurement signal processor 11. This adjusts, or sets, one or more control characteristics stored in the memory unit to place the impedance measurement signal processor 11 in the electrode test state. Adjustment of the one or more control characteristics stored in the memory unit causes adjustment of the gain characteristic of the amplifier module and adjustment of the conditioning function characteristics of the signal conditioning module to place the impedance measurement signal processor 11 in the electrode test state.

The defibrillator processor 13 sends at least one control signal to the impedance measurement signal generator 7 to cause it to generate an ac signal at a pre-determined voltage including a sine wave or a square wave and having a frequency in the range of approximately 30 kHz to approximately 64 kHz, preferably approximately 32 kHz. The ac signal is sent to the electrodes 3, and, as these form a capacitor, the ac signal passes through the electrodes 3. The electrodes 3 act to effect a change in the ac signal and the resultant changed ac signal, referred to as the electrode test ac signal, is passed to the protection circuit 9 and on to the impedance measurement signal processor 11.

The amplifier module of the impedance measurement signal processor 11 receives the electrode test ac signal from the electrodes 3 via the protection circuit 9, amplifies the signal and passes it to the signal conditioning module of the impedance measurement signal processor 11. The signal conditioning module carries out a number of conditioning functions, such as filtering and analogue to digital conversion, on the amplified electrode test ac signal. The electrode test ac signal is passed to the defibrillator processor 13.

The defibrillator processor 13 receives the electrode test ac signal from the impedance measurement signal processor 11 and analyses the electrode test ac signal to obtain an electrode test impedance signal. The defibrillator processor 13 then analyses the electrode test impedance signal to determine a pass or fail condition of the electrodes 3. Various methods may be used to determine a pass or fail condition of the electrodes 3. The defibrillator processor 13 may determine a pass condition if the electrode test impedance signal is within a pre-determined pass range and a fail condition if the electrode test impedance signal is above the pre-determined pass range. The pass range may be pre-determined by assessing an expected range of values of the electrode test impedance signal when the connectivity and electrical integrity of the electrodes is acceptable. The pre-determined pass range may be approximately 1 kΩ to approximately 5 kΩ. When the electrodes 3 are in a fail condition, a signal indicating an open circuit may be received by the defibrillator processor 13.

An electrode pass condition determines that the connectivity of the electrodes 3 via the connector studs 50 and the connecting wires 52 to a plug of the defibrillator 1 is intact and that the electrical integrity of each electrode 3 is within specification. An electrode fail condition may indicate inadequate connectivity of one or more of the electrodes 3. This may be due to, for example, improper connection between or a fault on any of the electrodes, electrode connecting wires and a plug of the defibrillator. A fail test result for the electrodes may indicate inadequate electrical integrity of one or more of the electrodes. This may be due to, for example, breakdown of gel of one or more of the electrodes, which is referred to as discontinuity of an electrode, or damage to one or more of the electrodes e.g. due to incorrect storage.

After an electrode test, when a pass condition for the electrodes 3 is determined, the defibrillator processor 13 may further process the electrode test impedance signal to determine an approximate age of the electrodes 3.

The defibrillator 1 may issue a message indicating an electrode pass condition or an electrode fail condition, such as an audible message and/or a visible message e.g. activation of a light, such as a light emitting diode (LED) indicator, provided on the defibrillator 1.

Methods according to the above-described examples can be implemented using computer-executable instructions that are stored or otherwise available from computer readable media. Such instructions can include, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can include hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

It is noted that any electrical component or device that is disclosed herein can include basic device components, such as a computer processor, a non-transitory computer readable storage medium or device that stores instructions which, when executed by the computer processor, cause the computer processor to perform certain functions as disclosed herein. Other hardware components, such as a display device, a bus between getting data from one component to another, input mechanisms, and so forth, are included as within the scope of this disclosure. Graphical user interfaces, multimodal interfaces, speech interfaces, gesture interfaces, text based interfaces, can also be utilized within the system or methods.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Any feature described in any embodiment or example can be combinable with any other feature of any other example or embodiment.

Although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

Claim language reciting "at least one of" refers to at least one of a set and indicates that one member of the set or multiple members of the set satisfy the claim. For example, claim language reciting "at least one of A and B" means A, B, or A and B.

What is claimed is:

1. An electrode test system of a defibrillator comprising: electrodes in a face-to-face test arrangement; an impedance measurement signal generator connected to the electrodes and configured to send an ac signal to the electrodes; an amplifier module that amplifies a signal according to a gain and comprising an adjustable gain characteristic; a signal condition module configured separately from the amplifier module and which comprises adjustable condition function characteristics independent of the gain, the adjustable condition function characteristics comprising one or more of filtering, analog-to-digital conversion and signal processing; an impedance measurement signal processor connected to the electrodes which is placeable in an electrode test state and configured to receive an electrode test ac signal from the electrodes and process the electrode test ac signal to obtain a processed electrode test ac signal; and a defibrillator processor connected to the impedance measurement signal generator and the impedance measurement signal processor, the defibrillator processor configured to place the impedance measurement signal processor in the electrode test state and to receive the processed electrode test ac signal, to analyze the processed electrode test ac signal to obtain an electrode test impedance signal and to analyze the electrode test impedance signal to determine a pass condition or a fail condition of the electrodes, wherein the defibrillator processor is configured to send at least one control signal to the impedance measurement signal processor to adjust one or more of the condition function characteristics of the signal conditioning module to place the impedance measurement signal processor in the electrode test state.

2. The electrode test system of a defibrillator of claim 1, in which the defibrillator processor is further configured to send at least one second control signal to the impedance measurement signal generator to cause the impedance measurement signal generator to send the ac signal to the electrodes.

3. The electrode test system of a defibrillator of claim 1, wherein the defibrillator processor is further configured to send the at least one control signal to the impedance measurement signal processor to adjust one or more characteristics of the amplifier module to place the impedance measurement signal processor in the electrode test state.

4. The electrode test system of a defibrillator of claim 3, wherein the defibrillator processor is further configured to send the at least one control signal to the impedance measurement signal processor to adjust the adjustable gain characteristic of the amplifier module to place the impedance measurement signal processor in the electrode test state.

5. The electrode test system of a defibrillator of claim 3, wherein the impedance measurement signal processor further comprises a memory unit and the defibrillator processor is configured to send the at least one control signal to the impedance measurement signal processor to adjust one or more control characteristics stored in the memory unit to place the impedance measurement signal processor in the electrode test state, and wherein the defibrillator processor is further configured to send the at least one control signal to the impedance measurement signal processor to adjust one or more control characteristics stored in the memory unit which adjusts one or more characteristics of the amplifier module to place the impedance measurement signal processor in the electrode test state.

6. The electrode test system of a defibrillator of claim 1, wherein the defibrillator processor is further configured to send the at least one control signal to the impedance measurement signal processor to adjust one or more of the conditioning function characteristics of the signal conditioning module to place the impedance measurement signal processor in the electrode test state.

7. The electrode test system of a defibrillator of claim 1, wherein the impedance measurement signal processor further comprises a memory unit and the defibrillator processor is configured to send the at least one control signal to the impedance measurement signal processor to adjust one or more control characteristics stored in the memory unit to place the impedance measurement signal processor in the electrode test state.

8. The electrode test system of a defibrillator of claim 1, wherein the impedance measurement signal processor further comprises a memory unit and the defibrillator processor is configured to send the at least one control signal to the impedance measurement signal processor to adjust one or more control characteristics stored in the memory unit to place the impedance measurement signal processor in the electrode test state, and wherein the defibrillator processor is further configured to send the at least one control signal to the impedance measurement signal processor to adjust one or more control characteristics stored in the memory unit which adjusts one or more of the adjustable condition function characteristics of the signal conditioning module to place the impedance measurement signal processor in the electrode test state.

9. The electrode test system of a defibrillator of claim 1, wherein each electrode is substantially planar and comprises at least one face, placed in the face-to-face test arrangement to form the capacitor.

10. The electrode test system of a defibrillator of claim 1, wherein each electrode of the electrodes is substantially planar and comprises a first face and a second face, wherein the first face of each electrode is provided by a dielectric liner of each electrode and is placed in the face-to-face test arrangement to form the capacitor.

11. The electrode test system of a defibrillator of claim 10, wherein a further dielectric is provided by one or more air gaps between the dielectric liners in the electrodes face-to-face test arrangement.

12. The electrode test system of a defibrillator of claim 1, wherein each electrode of the electrodes is substantially planar and comprises a first face and a second face, and wherein the second face of each electrode is provided by a substrate of each electrode and is placed in the face-to-face test arrangement to form the capacitor.

13. The electrode test system of a defibrillator of claim 1, wherein each electrode is substantially planar and comprises a first face and a second face and the first face of a first electrode is provided by a dielectric liner of the electrode and a second face of a second electrode is provided by a substrate of the electrode and the first face of the first electrode and the second face of second electrode are placed in the face-to-face test arrangement to form the capacitor.

14. The electrode test system of a defibrillator of claim 1, wherein the electrodes are located in a face-to-face test arrangement within a pouch.

15. The electrode test system of a defibrillator of claim 1, wherein the defibrillator processor determines a pass condition if the electrode test impedance signal is within a pre-determined pass range and a fail condition if the electrode test impedance signal is above the pre-determined pass range.

16. The electrode test system of a defibrillator of claim 15, wherein the pass range is pre-determined by assessing an expected range of values of the electrode test impedance signal when connectivity and electrical integrity of the electrodes is acceptable.

17. The electrode test system of a defibrillator of claim 15, wherein the pre-determined pass range is determined by testing of defibrillator electrodes in various states of connectivity and electrical integrity.

18. The electrode test system of a defibrillator of claim 1, wherein when the electrodes are in a fail condition, a signal indicating an open circuit is received by the defibrillator processor.

19. The electrode test system of a defibrillator of claim 1, wherein an electrode test is carried out on the defibrillator as part of an automatic defibrillator self-test process.

20. The electrode test system of a defibrillator of claim 1, wherein after an electrode test, when the defibrillator processor determines a pass condition for the electrodes, the defibrillator processor further analyses the electrode test impedance signal to determine an approximate age of the electrodes.

21. A method of testing electrodes of a defibrillator, the method comprising: using an impedance measurement signal generator to send an ac signal to electrodes; using an impedance measurement signal processor placeable in an electrode test state to receive an electrode test ac signal from the electrodes and to process the electrode test ac signal to obtain a processed electrode test ac signal; and using a defibrillator processor to send at least one control signal to the impedance measurement signal processor to change the impedance measurement signal processor from a non-test state to the electrode test state and to receive the electrode test ac signal, to analyze the processed electrode test ac signal to obtain an electrode test impedance signal and to analyze the electrode test impedance signal to determine a pass condition or a fail condition of the electrodes, wherein the impedance measurement signal processor further comprises a signal conditioning module independent of an amplifier module and the defibrillator processor is configured to send the at least one control signal to the impedance measurement signal processor to adjust one or more conditioning function characteristics of the signal conditioning module to place the impedance measurement signal processor in the electrode test state, wherein the conditioning function characteristics are independent of a gain and comprise one or more of filtering, analog-to-digital conversion and signal processing.

22. The method of testing electrodes in the defibrillator of claim 21, further comprising:
placing the electrodes in a face-to-face test arrangement to form a capacitor.

* * * * *